(12) United States Patent
Post

(10) Patent No.: US 8,317,807 B1
(45) Date of Patent: Nov. 27, 2012

(54) LARGE BORE VESSEL ACCESS AND CLOSURE DEVICE

(76) Inventor: Douglas Post, Santa Rosa, CA (US)

( * ) Notice: Subject to any disclaimer, the term of this patent is extended or adjusted under 35 U.S.C. 154(b) by 247 days.

(21) Appl. No.: 12/860,900

(22) Filed: Aug. 22, 2010

Related U.S. Application Data

(60) Provisional application No. 61/395,281, filed on May 10, 2010.

(51) Int. Cl.
*A61B 17/04* (2006.01)

(52) U.S. Cl. .......................................... 606/148; 606/190

(58) Field of Classification Search .................. 606/190, 606/148, 213; 604/164.01
See application file for complete search history.

(56) References Cited

U.S. PATENT DOCUMENTS

| | | | | |
|---|---|---|---|---|
| 5,527,322 A * | 6/1996 | Klein et al. | .................... | 606/144 |
| 6,036,699 A * | 3/2000 | Andreas et al. | ............... | 606/139 |
| 6,755,842 B2 * | 6/2004 | Kanner et al. | ................ | 606/148 |
| 7,736,372 B2 * | 6/2010 | Reydel et al. | ................. | 606/148 |
| 2002/0058910 A1 * | 5/2002 | Hermann et al. | .......... | 604/95.04 |

\* cited by examiner

*Primary Examiner* — Melanie Tyson
(74) *Attorney, Agent, or Firm* — Dergosits & Noah LLP

(57) ABSTRACT

A medical tool includes an access tool and a dissecting obdurator that is placed within a lumen of the access tool. The dissecting obdurator comprises a body having a first edge, a second edge and a cross section, the cross section having a height dimension measured from the first edge to the second edge and a width dimension perpendicular to the height dimension, the height dimension is two or more times the width dimension. The tip of the dissecting obdurator is selectively flexible and coupled to a distal end of the body, the selectively flexible tip being more flexible bending in the axis of the width dimension than bending in the axis of the height dimension.

13 Claims, 22 Drawing Sheets

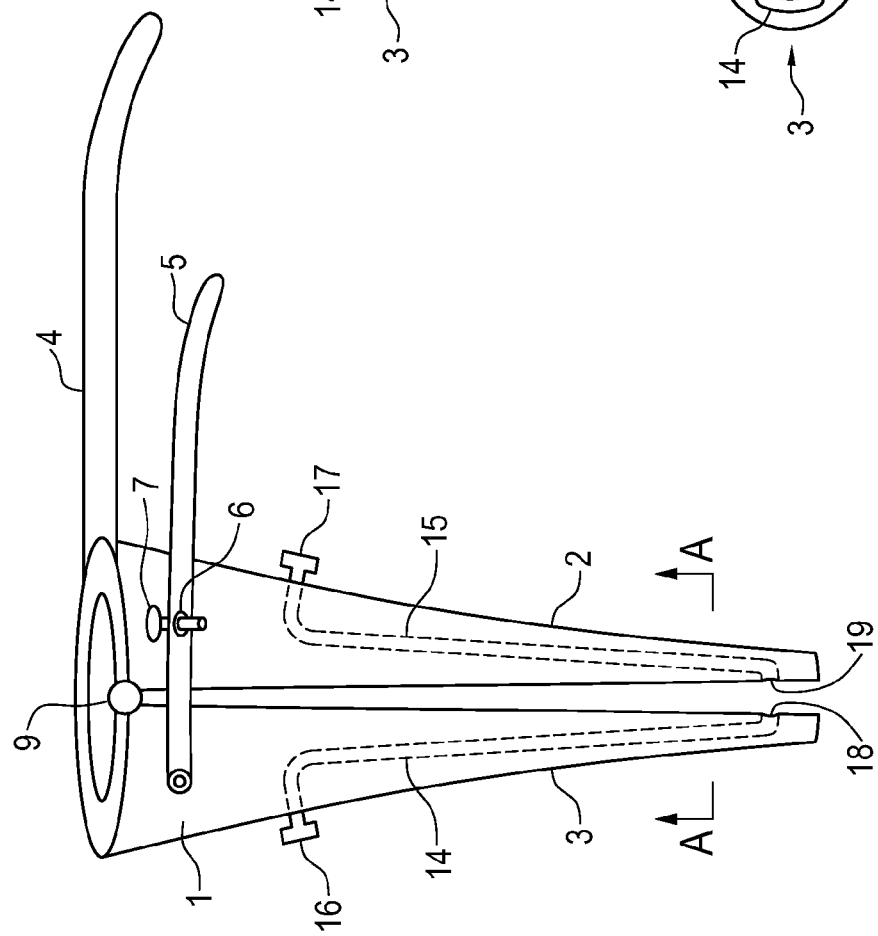
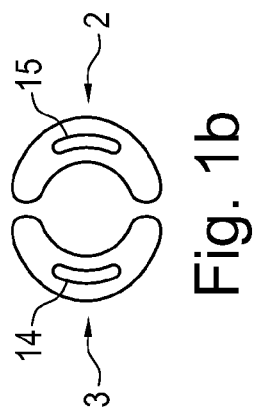
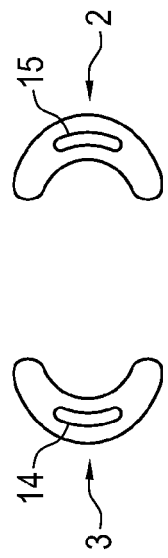

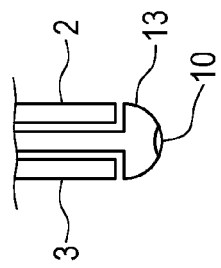
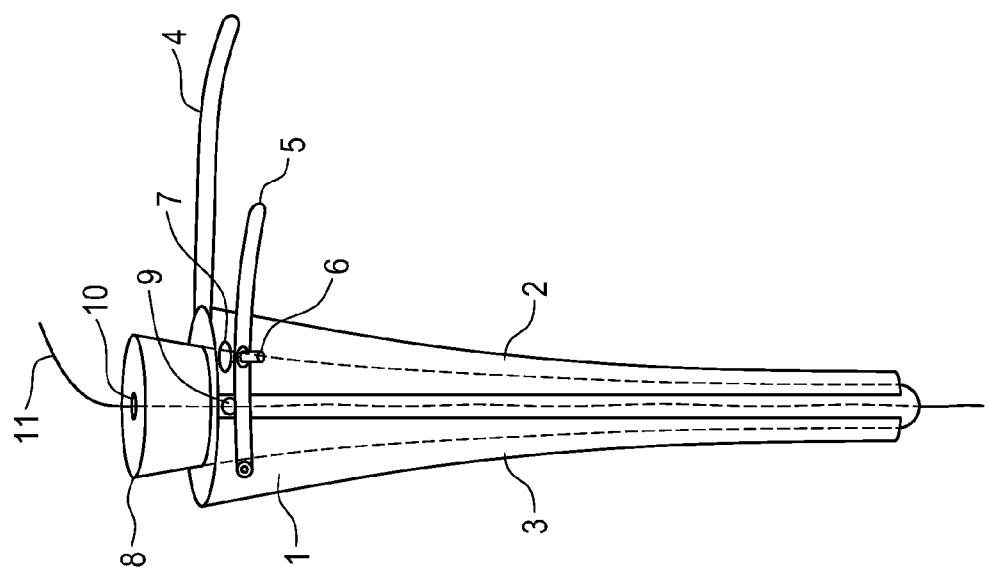

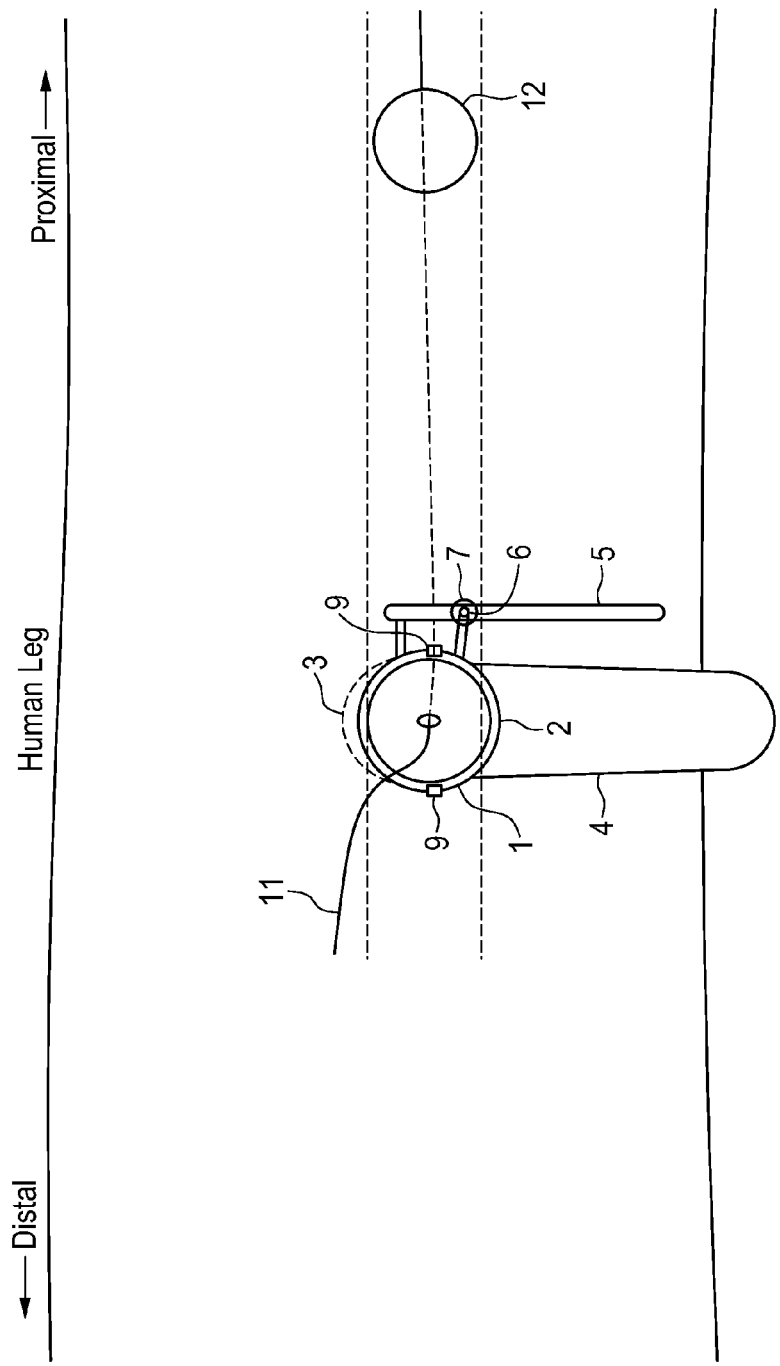

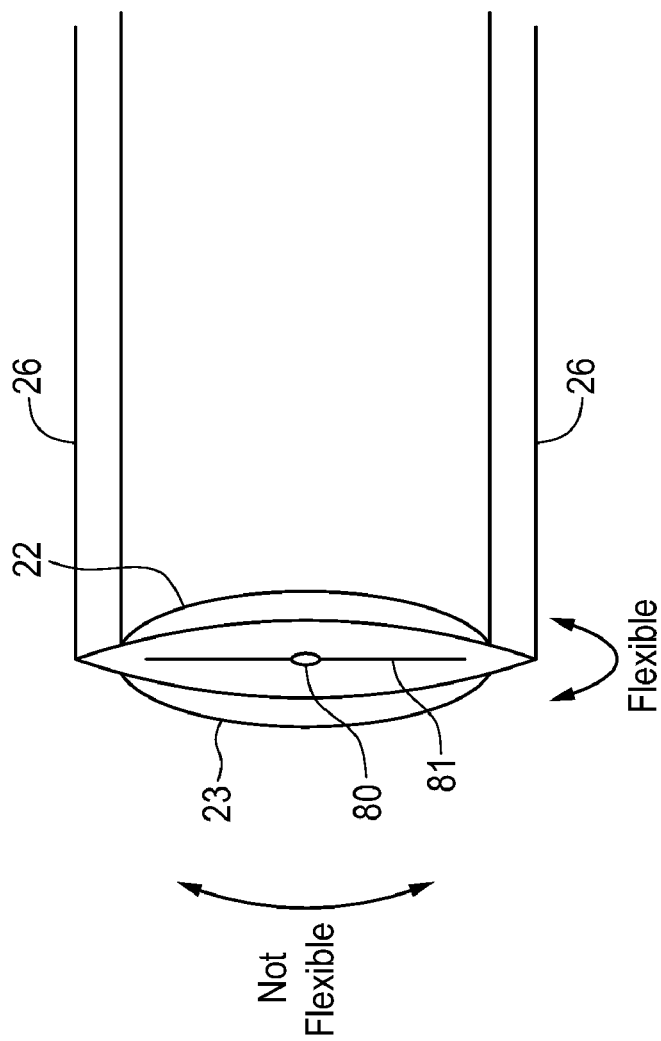

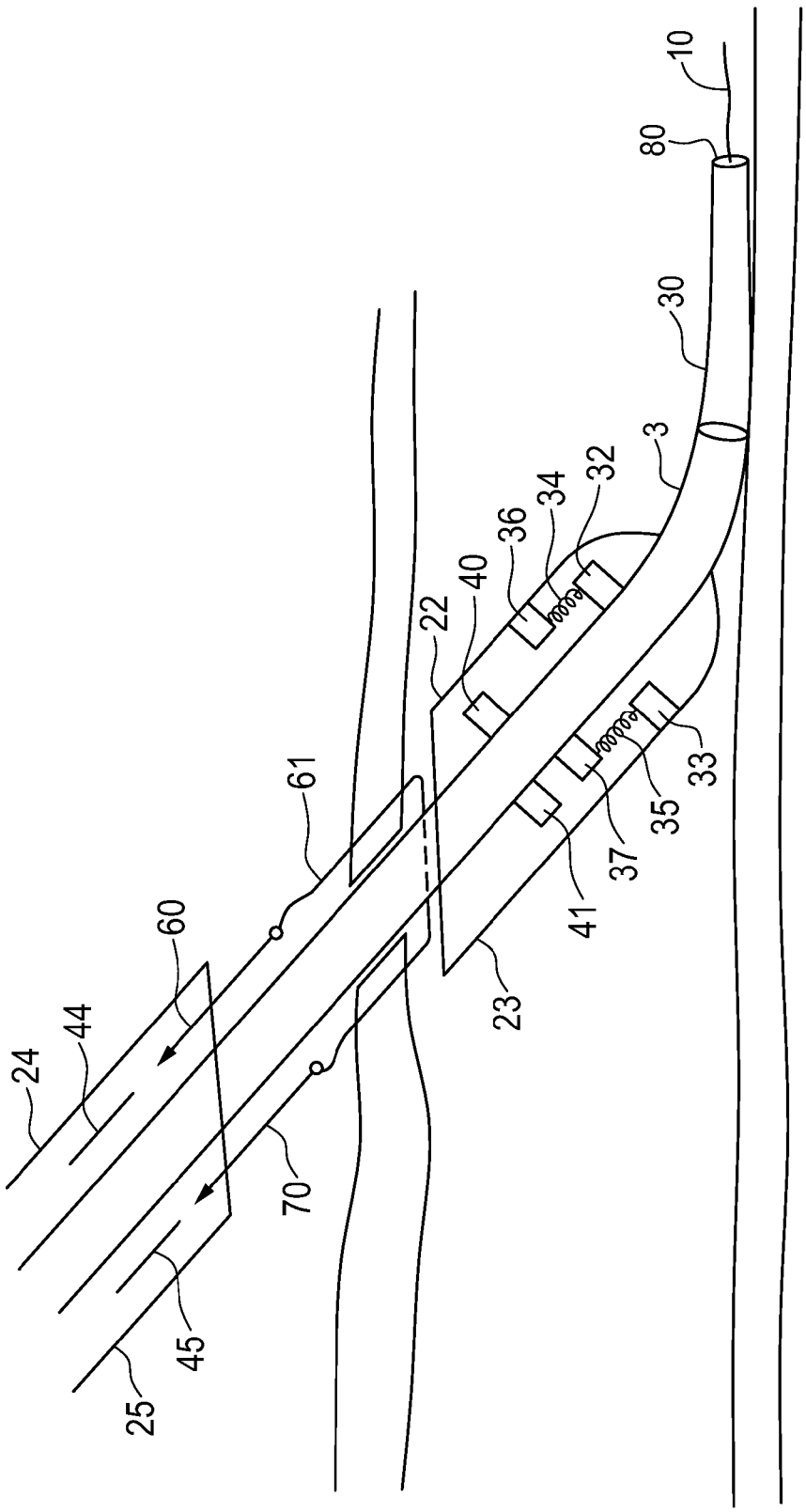

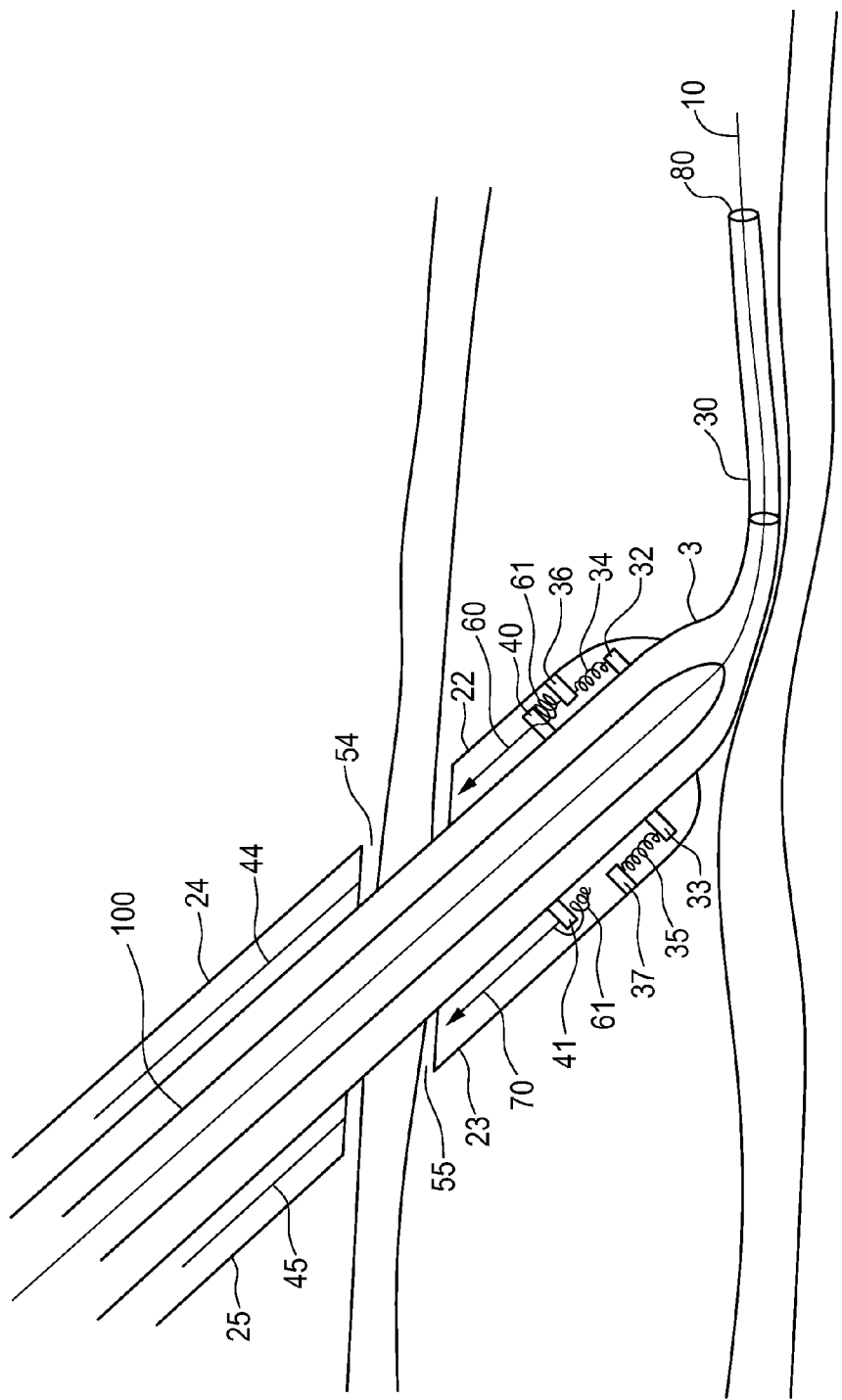

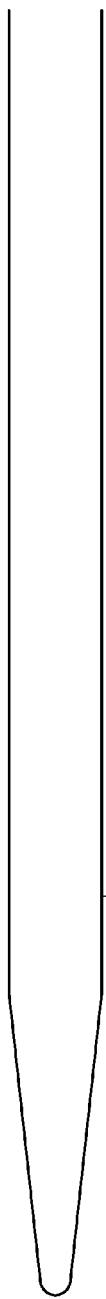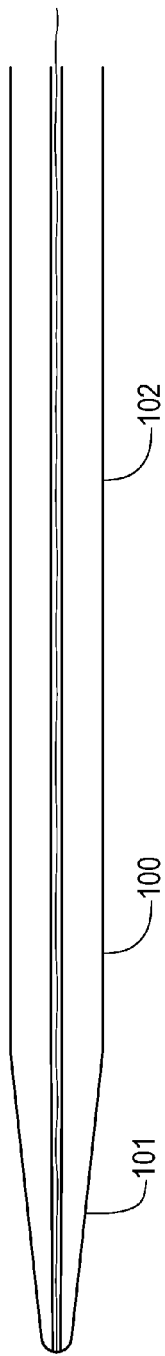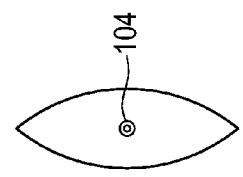
Fig. 9a
Fig. 9b
Fig. 9c

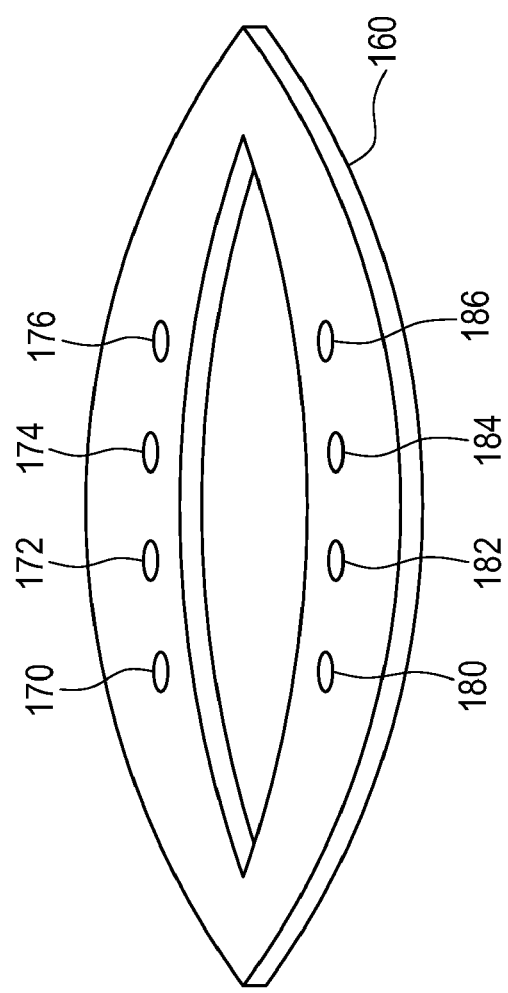

LARGE BORE VESSEL ACCESS AND CLOSURE DEVICE

CROSS REFERENCE TO RELATED APPLICATIONS

This patent application claims priority to U.S. Provisional Patent Application No. 61/395,281, "Large Bore Closure Concept" filed May 10, 2010 which is hereby incorporated by refrence.

BACKGROUND

Access to the patient vascular system is necessary for a wide variety of purposes in medicine, most often related to the diagnosis or treatment of the heart or the vascular system. For example, angioplasty balloons, coronary stents and percutaneous stent grafts for abdominal aortic aneurysms are often delivered to the arterial system while vena cava filters are often delivered to the venous system.

Typically devices are introduced to the vascular system using either surgical cut down techniques or percutaneous introduction techniques in which an opening is created in the wall of a vessel, frequently the femoral artery, that runs relatively close to the surface of the body.

Smaller devices (6-8 Fr) are typically introduced percutaneously and closed using either manual compression or with a closure device. One of many closure devices designed specifically for small arteriotomy openings may be used. These devices include clips, staples, automated suturing mechanisms, plugs made from collagen or other biologic materials, fillers, glues and the like. These devices have the advantage of speeding up recovery, reducing costs and decreasing the length of hospitalization.

Recent improvements in minimally invasive transvascular device therapy offer less invasive approaches to many new, significant vascular and cardiovascular medical problems but also require larger access sites. Examples of new therapies that fall into this category include percutaneous aortic valve replacement, percutaneous mitral valve repair, abdominal aortic valve stent graft therapy and acute cardiac support with percutaneously placed pumps. Below 12 Fr percutaneous techniques are typically used. In the 12-16 Fr range, either cut down or percutaneous approaches may be used and above 16 Fr. a surgical cut down is almost always used.

Each of these approaches presents the physician and patient with numerous challenges. Surgical cutdowns often require coordinating schedules with a second physician trained in these techniques, typically a surgeon. They incur the additional time and cost associated with this additional procedure as well as causing additional physical pain to the patient. Moreover, cut down techniques can be quite disruptive to the tissue involved.

Larger holes can be made percutaneously using the standard Seldinger technique followed by multiple, progressively larger obdurators—but this approach often leads to high rates of hematoma and other access site complications. When the standard Seldinger technique is used for initial access, a first needle and guidewire are followed by progressively larger dilators until an opening of sufficient size is created. This method of penetration of the vessel is traumatic to both the tissue tract and the vessel wall. Advancement of the obdurator exerts axial force on tissue and may cause injury to this tissue. The round, progressively larger obdurators used to open the artery leave behind a large, ragged and highly variable vessel opening. Because the opening is ragged, getting edge to edge alignment and apposition is difficult and achieving hemostasis is challenging.

The closure of small holes in vessels is an area that has seen much innovation and the prior art is extensive. The need to open and close larger holes is only now emerging with the development and growth of new therapies. Few specific solutions have been developed to address these needs.

Large size openings preclude most small vessel closure solutions for numerous reasons. Approaches like glues and plugs typically do not provide the mechanical strength required to pull and keep opposing vessel edges together when the opening is large and the vessel is under pressure. Suture based approaches are challenged by ragged, poorly defined, hard to locate vessel edges which make getting good attachment of the suture to the tissue difficult and subsequent closure very hard.

U.S. Patent Publication No. 2008/0208213 to Benjamin, discloses a means for opening as well as closing a large hole in an artery but does not disclose a means for accessing the artery through the tissue. Also, it discloses a traditional surgical cutting tool and an initial cutting procedure that includes numerous steps, requires considerable manipulation through a small opening and consists of a high degree of complexity. Moreover, the tools described are unlike those typically used by interventionalists and not likely to offer the familiarity and ease of use required for adoption.

A tool kit providing for access to the target artery or vein, a subsequent means for opening the artery in a controlled way and creating an opening with smooth edges and a consistent, characteristic easy to close shape would be desirable. Moreover, a means to prospectively load the edges of the opening with sutures or another means of closure such that easy closure is assured—prior to advancing subsequent devices through the opening—would be desirable.

Numerous unmet needs exist in this area. It would be preferable to replace the surgical procedure required to open the artery with a minimally invasive procedure that could be done by the interventionalist rather than requiring a surgeon and an operating room. Additionally, it would be preferable to provide for a more predictable, less traumatized vessel opening as part of gaining initial access to the artery or vein. It would be preferable that a device or tool kit should provide for access in vessels up to 10 mm in diameter and provide for subsequent closure with high ease of use. Other needs identified include avoiding the vessel pinching associated with some closure techniques and the possible flow disturbances and restenosis associated with this, to leave nothing but suture behind in vessel at the end of the procedure to avoid flow disturbances, to provide high reliability of closure and to provide high predictability of closure.

SUMMARY OF THE INVENTION

The present invention takes the form of a multi-component system consisting of a 1) vessel access tool with viewing mandrel for gaining access to the artery, 2) a flat or non-circular, flexible, self orienting, dissecting obdurator designed to easily open a well defined, appropriately shaped hole in the artery and 3) needle/suture assemblies attached to the dissecting obdurator such that the hole may be pre-loaded with sutures prior to starting the procedure.

Objects and advantages of this system include: 1) Minimally invasive access to the vessel. By introducing an expandable vessel access tool in its unexpanded state rather than introducing and withdrawing progressively larger obdurators, shear stress is minimized and a large, surgically created hole is not required. 2) A predictably shaped initial opening similar in shape to the transverse arteriotomy typically done by a vascular surgeon in a cut-down procedure is created. Smooth, predictably shaped edges are created such that grabbing and attaching devices or sutures can be done easily and predictably. 3) Easy loading of the vessel with sutures is provided. High ease of use and predictability are provided. 4) Easy closing of the vessel following removal of all devices at the end of the procedure is provided. 5) Technique and tools similar to those currently used by interventionalists are provided for hence reducing training needs and the likelihood of complications and misuse.

BRIEF DESCRIPTION OF THE DRAWINGS

FIGS. 1A-1F illustrate embodiments of a vessel access tool in side, cross section, tip detail and in use views;

FIGS. 2A-2C illustrate embodiments of a vessel access tool in place during placement of dissecting obdurator;

FIGS. 3A-3J illustrate embodiments of a flexible, non-circular, self orienting, transverse dissecting dilator and suture deployment assembly in various views;

FIGS. 6A-C illustrate embodiments of dissecting obdurators in side cross section views during use;

FIGS. 7A-B illustrate embodiments of dissecting obdurators with dilatation mandrel in side view cross section views in use;

FIGS. 9A-C: illustrate embodiments of obdurator dilatation mandrels; and

FIG. 10 illustrates a suture receiving and retention member.

DETAILED DESCRIPTION

List of Reference Numerals

Figure 1F:
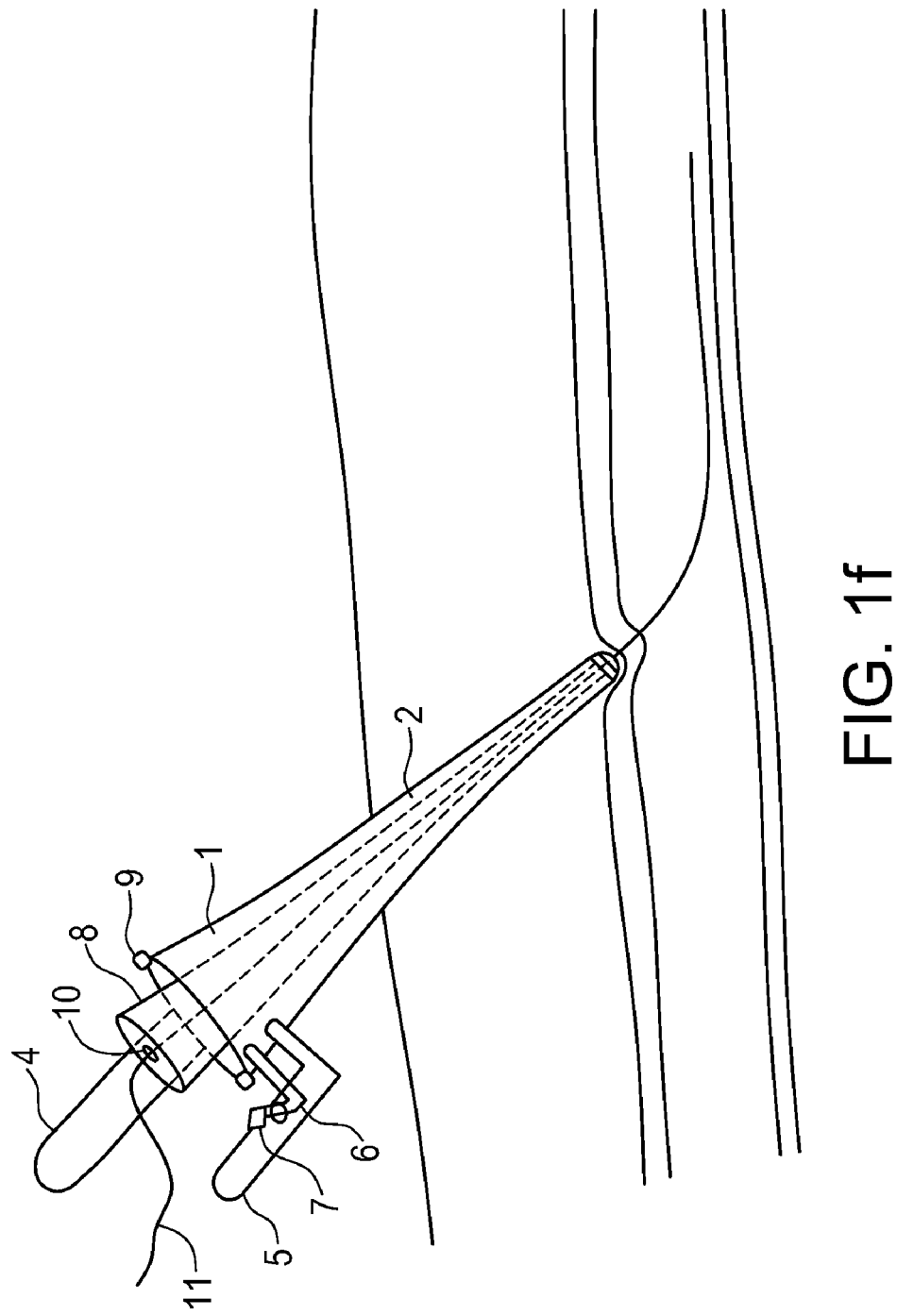

| 1 | Artery access Tool |
| --- | --- |
| 2 | Handle-side, spreader arm |
| 3 | Non-handle-side, spreader arm |
| 4 | Artery access tool handle |
| 5 | Artery access tool opening lever |
| 6 | Artery access tool bolt hole |
| 7 | Artery access tool opening bolt |
| 8 | Artery access tool clear viewing mandrel |
| 9 | Artery access tool hinge |
| 10 | Artery access viewing mandrel guidewire hole |
| 11 | Guidewire |
| 12 | Guidewire balloon |
| 13 | Viewing Mandrel Bulb |
| 20 | Dissecting obdurator |
| 22 | Distal, top needle/suture housing |
| 23 | Distal, bottom needle/suture housing |
| 24 | Proximal, top needle receiver housing |
| 25 | Proximal, bottom needle receiver housing |
| 26 | Dissecting obdurator edge |
| 30 | Selectively flexible obdurator tip |
| 31 | Selectively flexible obdurator body |
| 32 | Top obdurator body leaflet spring bracket |
| 33 | Bottom obdurator body leaflet spring bracket |
| 34 | Top obdurator leaflet spring |
| 35 | Bottom obdurator leaflet spring |
| 36 | Top needle protector leaflet spring bracket |
| 37 | Bottom needle protector leaflet spring bracket |
| 38 | Obdurator body, tapered section |
| 40 | Top needle holding bracket |
| 41 | Bottom needle holding bracket |
| 44 | Top needle receiver #1 |
| 45 | Bottom needle receiver #1 |
| 46 | Top needle receiver #2 |
| 47 | Bottom needle receiver #2 |
| 48 | Top needle receiver #3 |
| 49 | Bottom needle receiver #3 |
| 50 | Top needle receiver #4 |
| 51 | Bottom needle receiver #4 |
| 54 | Top Vessel Capture Slot |
| 55 | Bottom Vessel Capture Slot |
| 60 | Top Needle 1 |
| 61 | Suture #1 |
| 62 | Top Needle 2 |
| 63 | Suture #2 |
| 64 | Top Needle 3 |
| 65 | Suture #3 |
| 66 | Top Needle 4 |
| 67 | Suture #4 |
| 70 | Bottom Needle 1 |
| 72 | Bottom Needle 2 |
| 74 | Bottom Needle 3 |
| 76 | Bottom Needle 4 |
| 80 | Obdurator Guidewire Lumen |
| 81 | Split to Open Obdurator Lumen |
| 83 | Obdurator Guidewire Slotted Lumen |
| 90 | Top suture attachment housing member |
| 91 | Top suture attachment housing slot |
| 92 | Bottom suture attachment housing member |
| 93 | Bottom suture attachment housing slot |
| 100 | Obdurator dilating member |
| 101 | Obdurator dilating member tapered tip |
| 102 | Obdurator dilating member shaft |
| 103 | Obdurator dilating member guidewire hole |
| 110 | Top needle receiver fluted port #1 |
| 112 | Top needle receiver fluted port #2 |
| 114 | Top needle receiver fluted port #3 |
| 116 | Top needle receiver fluted port #4 |
| 120 | Obdurator suture slot #1 |
| 122 | Obdurator suture slot #2 |
| 124 | Obdurator suture slot #3 |
| 126 | Obdurator suture slot #4 |
| 130 | Bottom needle receiver fluted port #1 |
| 132 | Bottom needle receiver fluted port #2 |
| 134 | Bottom needle receiver fluted port #3 |
| 136 | Bottom needle receiver fluted port #4 |
| 140 | Device or sheath |
| 150 | Dissecting Obdurator Tip Inner Liner |
| 151 | Dissecting Obdurator Tip Nitinol Hypotube |
| 152 | Dissecting Obdurator Tip Hypotube Slots |
| 153 | Dissecting Obdurator Tip Outer Sleeve |
| 160 | Suture receiving and retention member |
| 170 | Bottom Needle 1 receiving and retention hole |
| 172 | Bottom Needle 2 receiving and retention hole |
| 174 | Bottom Needle 3 receiving and retention hole |
| 176 | Bottom Needle 4 receiving and retention hole |
| 180 | Top Needle 1 receiving and retention hole |
| 182 | Top Needle 2 receiving and retention hole |
| 184 | Top Needle 3 receiving and retention hole |
| 186 | Top Needle 4 receiving and retention hole |

Referring now to FIGS. 1a-f, an embodiment of the vessel access tool, a speculum-like tissue spreading device is shown in side view in FIG. 1a. The vessel access tool 1 may consist of a handle 4, a handle-side spreader arm 2 and a non-handle side spreader arm 3, an opening lever 5 that can be moved relative to the handle 4 in order to open the spreader arms as needed. When pushed down relative to the handle 4, the spreader arms articulate open at the hinge 9. The opening lever 5 can be held in this open position by tightening the opening bolt 7 as a result of screwing it into the bolt hole 6. In other embodiments, any other suitable mechanism may be used to hold the opening lever 5 in the open position.

Notable features of this tool can include a tapered shape designed to prevent blunt trauma as the tool cannulates the tissue and the length of the spreader arms. While the required length will depend on the depth of tissue to be penetrated, for femoral access in normal weight people, a tissue depth of 2-4 cm is generally sufficient. It is preferred to keep the access tool only slightly longer than the tissue depth in order to facilitate access to the vessel and manipulation of devices through it. For most people, a tool length of 3-5 cm will be adequate. Notably, the access tool is delivered over the guidewire 11 subsequent to cannulation using a needle as part of the Seldinger technique. An estimate of the length needed can be made based on the depth of penetration required for the initial needle to get vessel access. To access other vessels or tissue structures, different lengths may be required and, in some very obese people, this method may be contraindicated due to the inability to manipulate subsequent tools and devices through a very long access tool.

Additionally, the spreader arms are designed such that, in the closed position, the tip of the access tool has a cross sectional diameter preferably not more than 3 mm in diameter as shown in FIG. 1b and, in the open position, a preferable width can be between 6 and 10 mm with the exact width dependent on the size of the artery being accessed. It is preferred that the access tool should achieve an inner arm to arm dimension slightly larger than the vessel diameter.

FIG. 1d shows how the viewing mandrel 8 may sit between the spreader arms during initial cannulation and shows the how the guidewire 11 can pass though the guidewire lumen and hole 10. The viewing mandrel can preferably be constructed of a clear, rigid, biocompatible polymer such as a polycarbonate such that the color and general morphology of the tissue being cannulated could be visibly discerned through the mandrel. The mandrel can be held in place compressibly between the spreader arms and would preferable include a bulbous tip 13 in order to facilitate cannulation. The concave surface can also function as a lens collecting the maximum amount of ambient light. The body of the mandrel can be tapered and sized to fill the void to between the spreader arms as shown in FIG. 1d.

Notably, the vessel access tool device configuration is the simplest of the large, well known group of speculum and speculum-like devices. Features typical of the group of devices are clearly applicable to this method and apparatus. The operation and applications of the vessel access tools are well known to one of ordinary skill in the art. Various known design form factors can be utilized in the present invention. For example, in an embodiment, the form factor of a pistol grip handle can be integrated into the vessel access tool for physician ease of use. In another embodiment, the speader arms of the access tool can move slideably relative to one another rather than by a hinge. Vibrational motion might be imparted to the access tool as well in order to facilitate ease of cannulation. A biocompatible lubricant might be used as well on the outside surface of the access tool in order to facilitate access.

Referring now to FIG. 1f, the vessel access tool 1 is shown in place following tracking of the device over the guidewire 11. In order to prevent unacceptable blood flow during subsequent steps, it is intended that the guidewire 11 should be balloon tipped 12. Depending on the specific, individual anatomy, it may not be necessary to use a balloon tipped guidewire 11, if blood flow can be stopped proximally by other means. For example, a simple tourniquet or tourniquet like device or other device can be used to stop the blood flow. Much of this will depend on the body habitus of the person being treated with manual compression being more effective in smaller or thinner individuals.

Referring now to FIG. 3a-j, the flexible, non-circular, dissecting obdurator 20 is shown. The device may comprise multiple components: the selectively flexible obdurator tip 30, the selectively flexible obdurator body 31, the tapered section of the obdurator body 38, a dissecting edge 26, a guidewire lumen 80 or guidewire slot 83, a split to open obdurator lumen 81, a top distal needle/suture housing 22, a bottom distal needle/suture housing 23, a top proximal needle/suture housing 24, a bottom proximal needle/suture housing 25, a top vessel capture port 54 and a bottom vessel capture port 55.

Figure 2A:
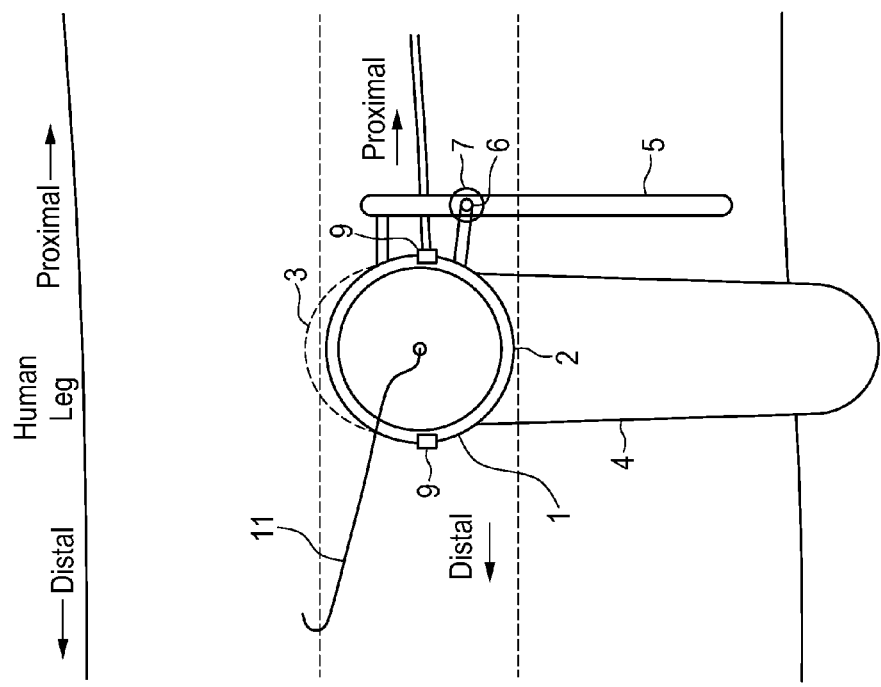
Figure 2C:
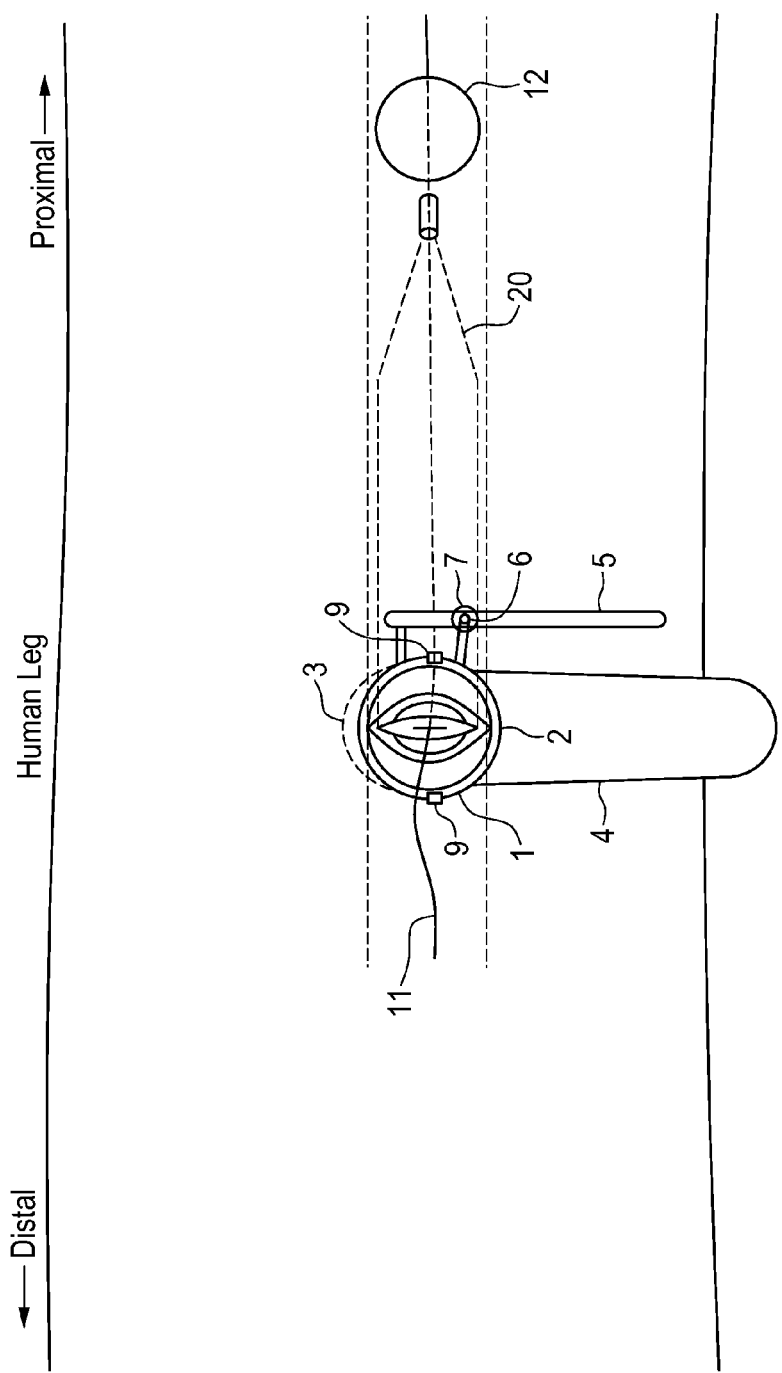
Figure 3A:
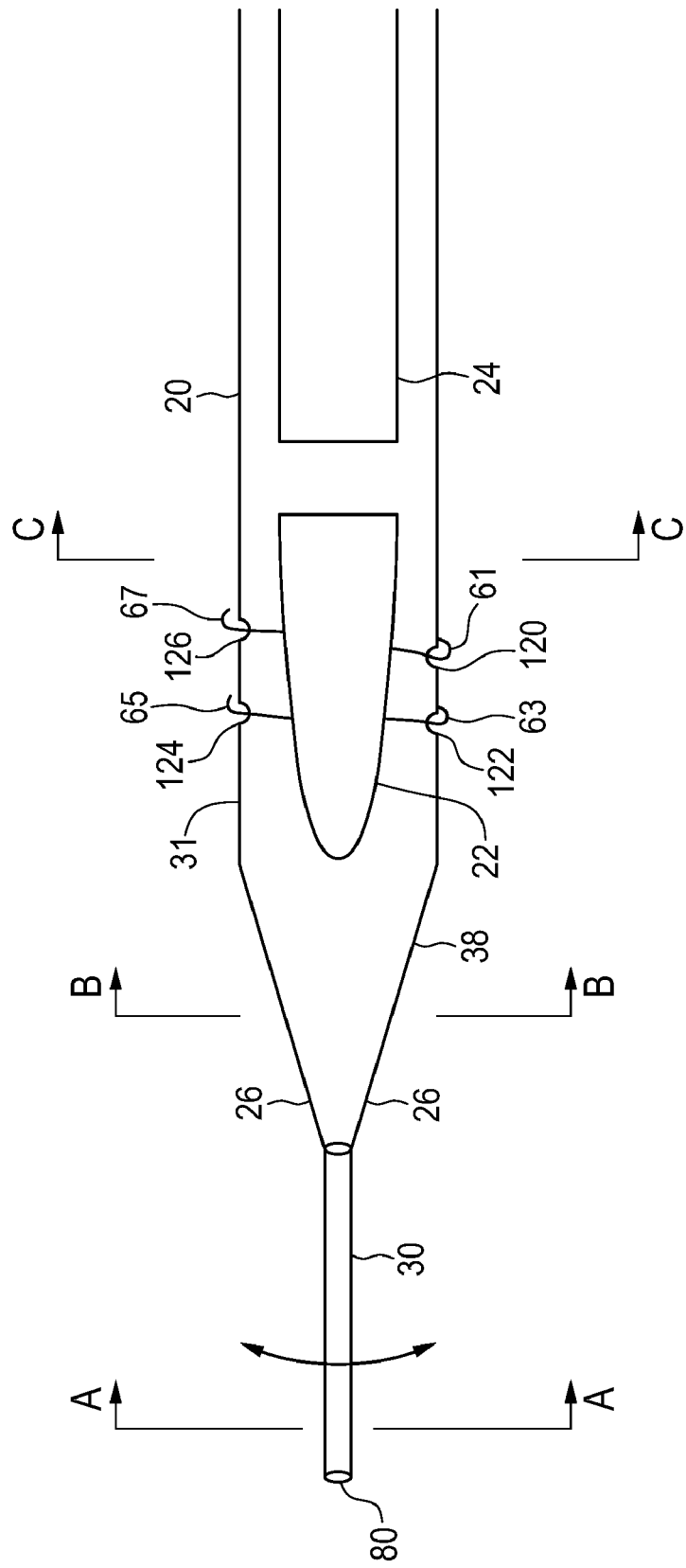
Figure 3B:
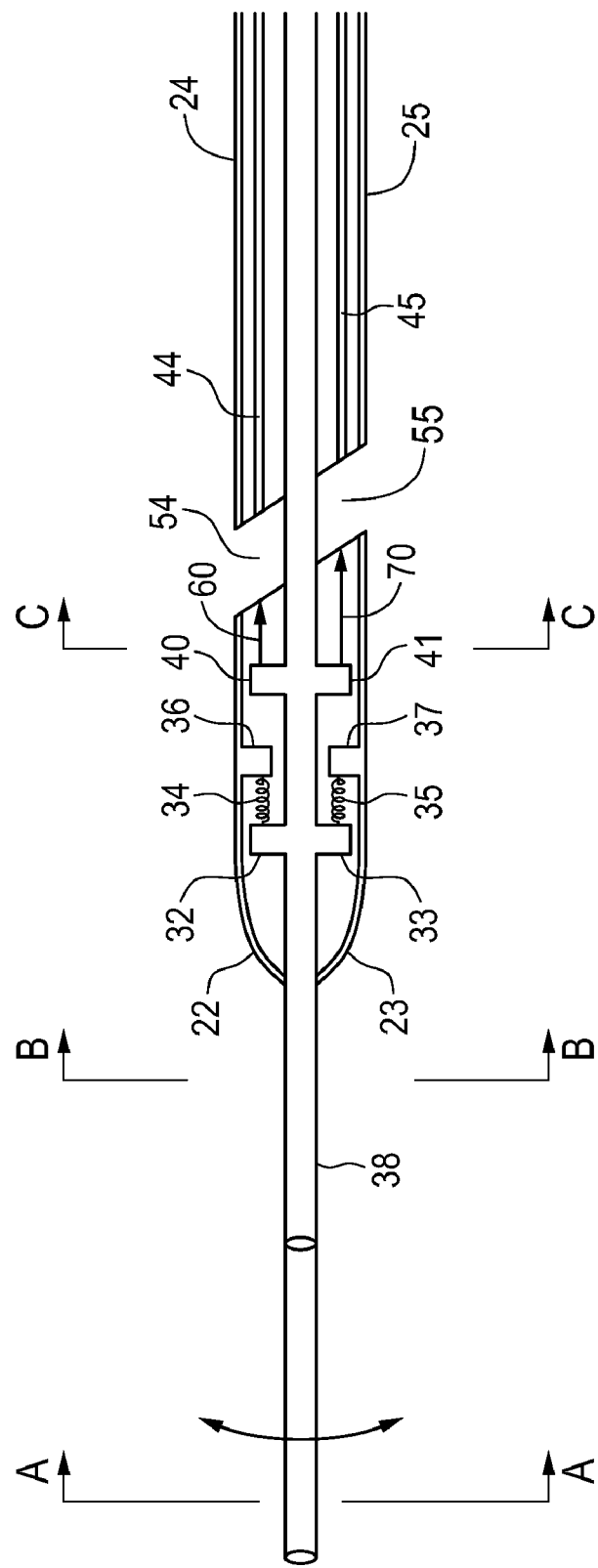
Figure 3C:
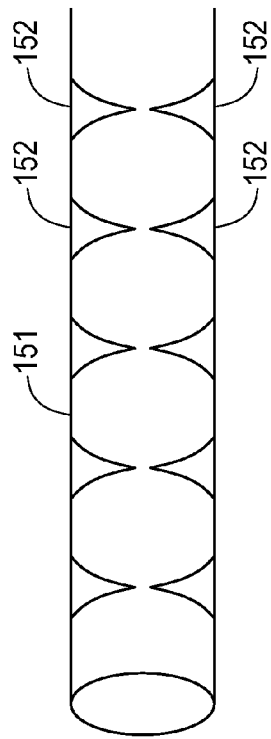
Figure 3D:
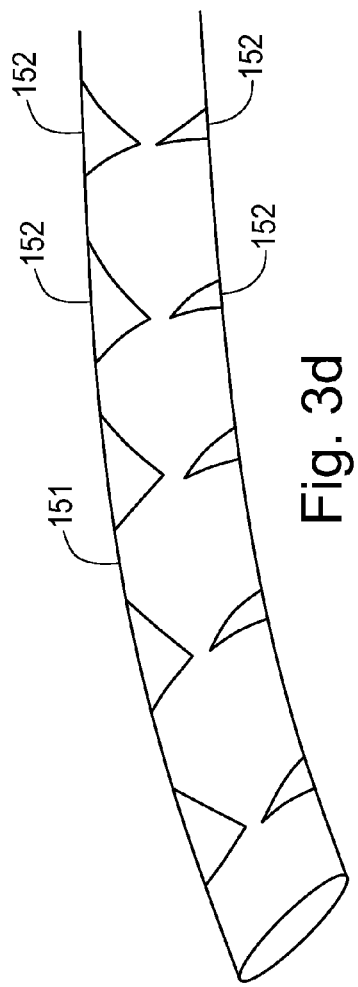
Figure 3E:
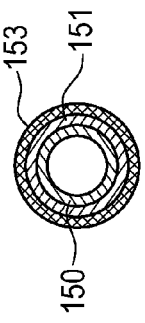
Figure 3H:
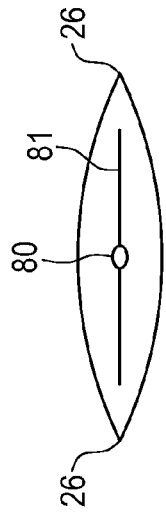
Figure 3I:
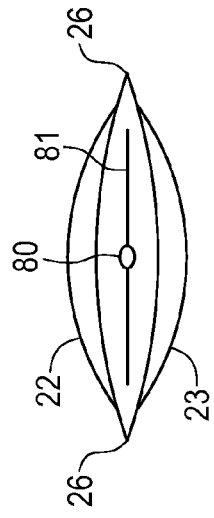
Figure 3F:
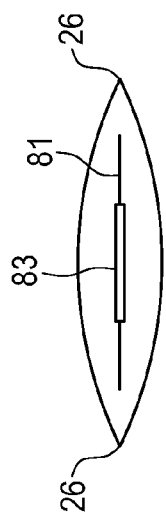
Figure 3G:
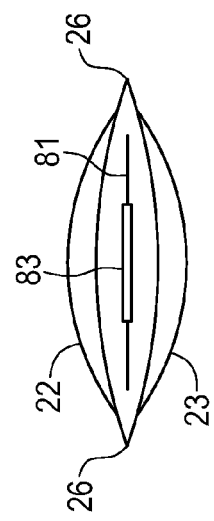

The selectively flexible tip 30 and body 31 are designed to bend in a plane such that dissecting obdurator 20 may orient itself or can easily and predictably be oriented with the flat, dissecting body 31 of the obdurator 20 entering the vessel at a transverse angle as shown in FIG. 2c. This is accomplished by constructing the dissecting obdurator tip 30 and body 31 with bending moments that vary depending on the plane, making it selectively flexible. Specifically, the tip 30 and body 31 are most flexible in a plane running substantially along the long axis of the device and approximately perpendicular to a plane of the widest feature of the dissecting obdurator body as shown in FIG. 3a which is a top view and FIG. 3b which is a side view. More specifically, the selective flexibility can be provide more flexibility for up and down movement of the obdurator body 38 and less flexibility for side to side movement. The selective flexibility can be accomplished by various means. In an embodiment, the tip 30 may be constructed of a nitinol hypotube 151 machined with wedge like voids or grooves 152 arranged along the length of the tip 30. The voids or grooves 152 can extend in a direction that is substantially perpendicular to the plane of the more flexible movement as shown in FIG. 3c. When a bending moment is applied, the wedges or grooves 152 preferentially bend in the plane of desired flexibility. Alternately, in other embodiments, wire or fiber braiding patterns may be used to get this same effect as may other hypotube patterns or catheter construction techniques. In an embodiment, the tip 30 of a typical guide or micro catheter construction as shown in FIG. 3e may comprise: a lubricious inner layer 150 preferably constructed of PTFE, a hypotube 151 or wire braided layer around the inner layer 150 and an outer layer 153 around the hypotube 151. The outer layer 153 can be a tubular structure consisting of one of the commonly used medical device polymers.

As can be seen in FIGS. 3f-3j, the selectively flexible obdurator body is naturally most flexible along the plane of its short cross sectional axis by virtue of its cross sectional geometry and the lower second moment of area apparent along that axis. Preferably the ratio of height (y-axis, FIG. 3j) to width (x-axis, FIG. 3j) can be 2 to 1 or more in order for the obdurator to provide good, selective dissection. In an embodiment, the height to width ration can be less than 5 to 1. More generally, the body 31 of the dissecting obdurator 20 is constructed of a medical grade polymer that provides the required flexibility. The tip 31 is preferably of a diameter similar to a typical microcatheter, 2.0-5.0 Fr in diameter as is the width (x-axis, FIG. 3j). The height (y-axis, FIG. 3j) will depend on the size of the opening to be made and is expected to be in the range of 12-30 Fr for a typical femoral artery.

Figure 6A:
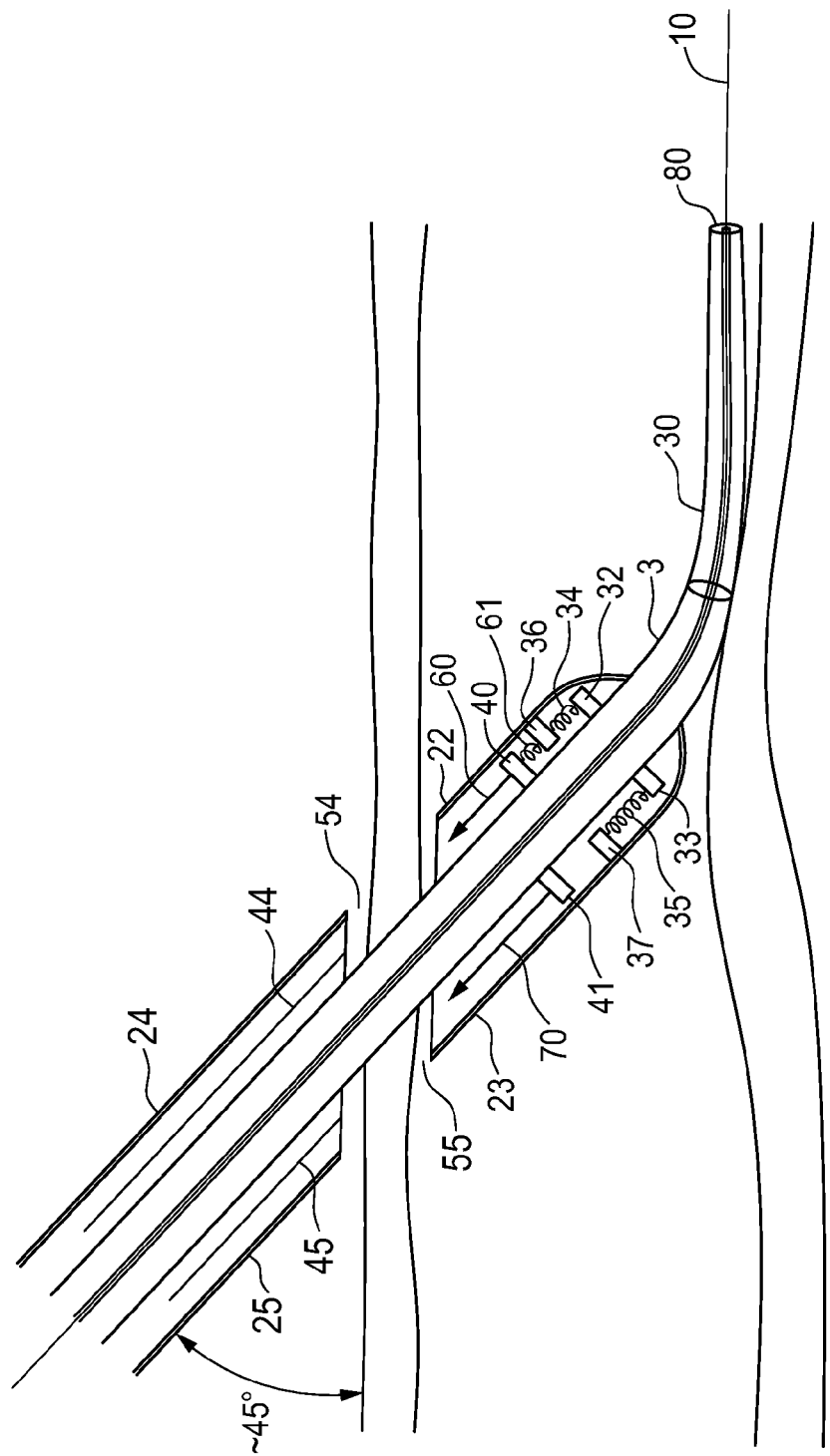

The benefit of the selectively flexible tip 30 and the access tool 1 are that they can provide self orientation or easy, predictable orientation of the dissecting obdurator body 31 into the plane most suitable for an incision, i.e. the plane transverse to the artery as shown in FIG. 2c. This occurs because, as seen in FIG. 6a, the dissecting obdurator 20 makes a 30-45 degree turn immediately upon entering the artery. The selective flexibility of the tip 30 enters the artery and bends. The tip 30 will bend in the more flexible direction and allows the operator to know when the obdurator 20 is properly oriented by force feedback. When the tip 30 is oriented with its more flexible axis perpendicular to the transverse plane, the tip 30 will move within the artery with less resistance. Furthermore, the access tool 1 eliminates the shear stress that adjacent tissue normally exerts on an obdurator and eliminates the rotational force exerted on a body passing through muscle and tissue at an angle contrary to the directional orientation or grain of the tissue. A substantial benefit of this approach is automatic alignment for easy creation of a transverse incision in the vessel. The shape of the transverse incision is advantageous for subsequent loading with sutures and that is typical of the type of incision created by vascular surgeons when they access the vessel surgically.

The selective flexibility of the dissecting obdurator is critical to its operation and unique to this device. As can be discerned elsewhere, orienting the tip 30 of the dissecting obdurator properly is essential to providing for entry of the tapered section 38 into the artery in the transverse plane and, hence, an appropriate arteriotomy. The selective flexibility feature is effective because of the considerable focus that interventionalists place on catheter skills and their notable ability to discern relatively small differences in resistive force. For example, interventionalists report being able to discern difference between different brands of coronary stents, which in vivo data shows have differences in mean track force of approximately 0.2 N. Other notable examples of the importance of force feedback and tactile sensation tools for the interventionalist come from the fields of medical device simulation, guidewire selection and physician training. In medical device simulator design, simulation of accurate force feedback, i.e. haptics is an important area and much modeling is going on to model the various factors contributing to force feedback accurately because of the importance of this to physicians in creating a realistic experience. In guidewire selection, doctors report considerable differences in guidewire trackability even though the absolute forces are very low showing that small difference can be discerned. Finally, in physician training, it is not unusual for many cases to be required for a physician to be considered qualified in a new procedure with a specific emphasis often placed on catheter skills. For example, JACC standards require an interventionalist to do 25 carotid stenting cases to be considered qualified showing just how much focus there is on strong catheter skills.

Based on data from coronary stenting showing a high degree of physician tactile sensitivity, it is preferable that the resistive track force of the selectively flexible tip 30 be 0.1 N or greater less when the tip 30 and tapered section 38 are advanced in the proper, transverse plane than when advanced more than 10 degrees out of this plane because of the criticality of getting the orientation correct and the dependence of this on the selective flexibility feature. Notably, one reason the tip 30 is round is in order to best provide for rotation in vivo and allow the physician to easily find the axis of least resistance.

In a preferred embodiment, the dissector body 31 has a tapered section 38 that can help to dissect the vessel as the dissector body 31 is pushed into the artery. The top 22 and bottom 23 suture/needle housing assemblies may be located on the tapered part of the obdurator body 38 but are preferably proximal to the tapered section. As the housings will add some rigidity, it is advantageous to place the top 22 and bottom 23 suture/needle housing assemblies proximal to the taper so as not to interfere with the dissection process. The housings assemblies preferably have a low profile to keep the cross section and second moment of area as low as possible.

In an embodiment, the dissecting obdurator edge 26 needs to be sufficiently sharp so that its entry into the vessel creates a clean dissection along the transverse plane of the vessel. The dissecting obdurator edge 26 is advantageous in design in comparison to the typical round obdurator. Rather than the clean transverse incision made by the dissecting obdurator edge 26, a round obdurator inherently cannot make a directional incision and may only produce an uncontrolled incision. The sharp edge preferably has a surface described by a radius of curvature in the range of 0.01 mm or less to 1 mm in order to effectively dissect the artery.

The dissecting obdurator 20 is directed over the guidewire 11 by running the guidewire 11 through the guidewire hole 80. Alternately, a guidewire slot 83 may be provided in order to manually center the dissecting obdurator 20 when the guidewire 11 is initially biased to one side of the artery or the other which often happens in clinical practice. In an embodiment, the guidewire slot 83 can be tapered such that it is circular or narrow distally and wider proximally. The guidewire slot 83 is preferably 30-80% of the width of the obdurator body in the tapered section. This allows the physical to center the obdurator by using direct visualization and allow for the centering of the tapered section of the obdurator in the middle of the vessel as the dissecting obdurator 20 is advanced.

Figure 4A:
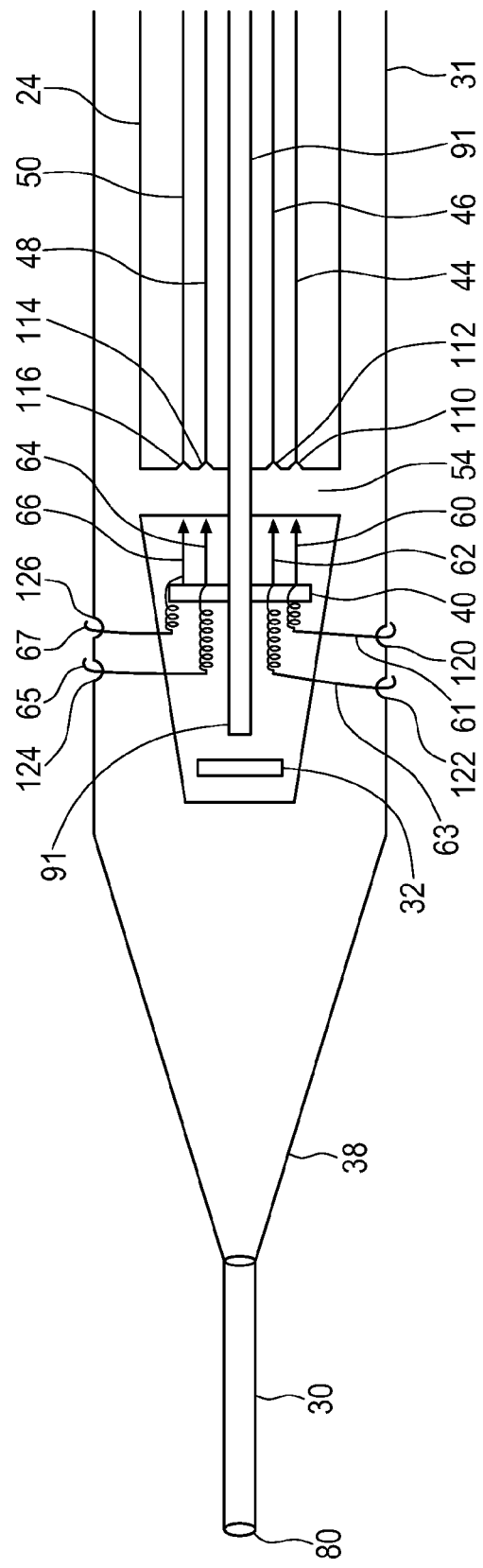
FIGS. 4A-4B illustrate embodiments of dissecting obdurators in top and bottom cut-away views.
Figure 4B:
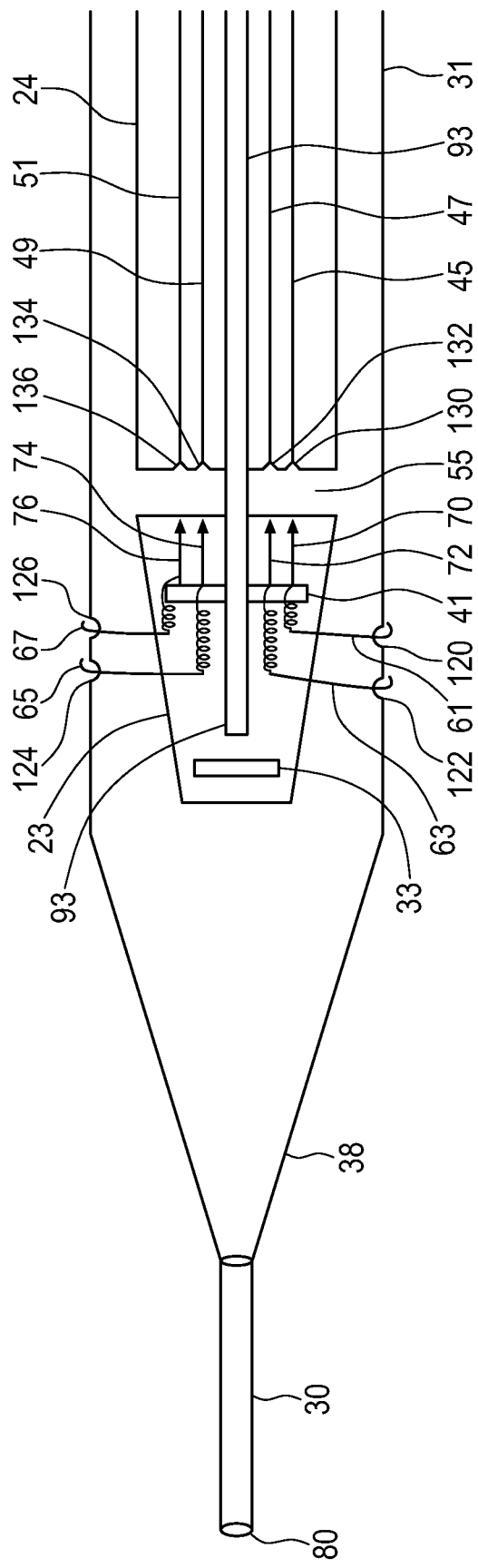
Figure 5A:
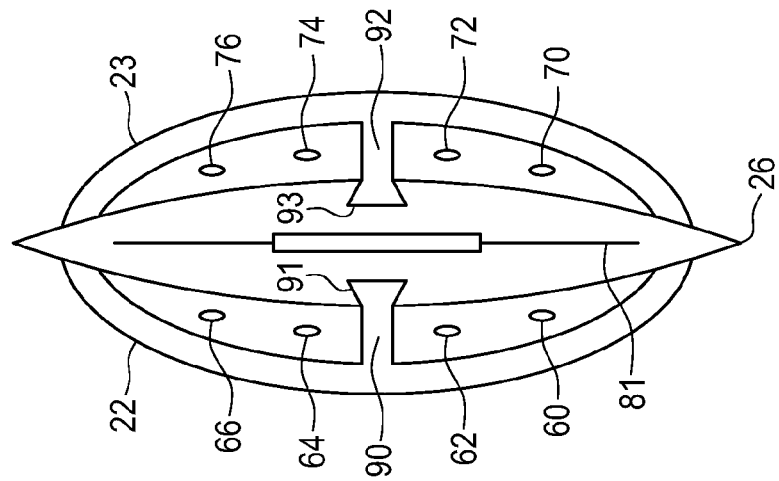
FIGS. 5A-5B illustrate embodiments of cross sections of a dissecting obdurator.
Figure 5B:
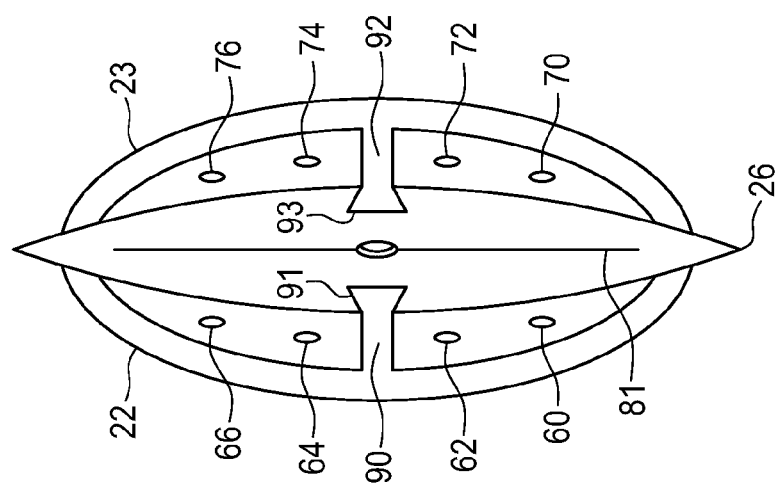

Referring now to FIG. 4a, the top of the dissecting obdurator 20 is seen with the suture/needle housing 22 cut away. The low profile, needle/suture deployment modules 22 and 23 can be located distally along the top and bottom of the obdurator 20 and separated from the proximal receptor modules by the vessel capture slots 54 and 55. The intent of the needle/suture deployment modules 22 and 23 are to contain the needles and sutures in a configuration suitable for deployment upon activation. In a preferred embodiment, 2-4 needles 60, 62, 64 and 66 are mounted on brackets 40 and 41, with the sharp ends pointing proximally. Attached to the distal ends of the needles are standard sutures. The matching pairs of needles are attached to the opposite ends of sutures 61, 63, 65 and 67 with lengths of coiled suture stored in the housings. Notches 120, 122, 124, 126 for suture passage go from one side to the other.

Matching needle/suture receptor modules 24 and 25 can be located along the top and bottom of the obdurator 20 proximal to the deployment modules 22 and 23. The receptors 24 and 25 are designed to mate up and accept the needles 60, 62, 64 and 66 upon compression of the needle/suture deployment modules 22 and 23 and the needle/suture receptor modules 24 and 25. The needle/suture receptor modules may incorporate funnel shaped receptor ports 110, 112, 114 and 116 that are aligned with each of the needles 60, 62, 64 and 66. The ports 110, 112, 114 and 116 are located directly proximal to the needles 60, 62, 64 and 66 such that a direct line is created between each needle 60, 62, 64 and 66 and its respective receptor port 110, 112, 114 and 116. The ports 110, 112, 114 and 116 can have a funnel shape that is sufficiently wide, preferably 0.5 mm or more such that any unpredictable bias that may occur as needles 60, 62, 64 and 66 pass through tissue may be accommodated. Thus, even slightly misaligned needles 60, 62, 64 and 66 will still be predictably received by the receptor ports 110, 112, 114 and 116. Preferably the needles 60, 62, 64 and 66 are barbed and the receptor funnel designed with a proximal diameter just smaller than the needle 60, 62, 64 and 66 diameter and with a grating type finish or a soft polymeric finish such that upon entry of the needle 60, 62, 64 and 66 into the ports 110, 112, 114 and 116 compression fits occur.

With reference to FIG. 6a, the vessel access slot 54 and 55 is designed to accept the edge of the just dissected vessel upon advancement of the dissecting obdurator 20. The vessel access slot 54 and 55 is preferably 1-3 mm in width and oriented at an angle to longest axis of the dissecting obdurator 20 as shown in FIG. 6a. In a preferred embodiment, the slot 55 is preferably positioned at an angle of 20-60 degrees to the main axis, depending on the angle of entry selected for the initial Seldinger approach. In some embodiments, it may be advantageous to have a more oblique angle of entry, i.e. 30% or less due to the large size and rigidity of the dissecting obdurator and, more importantly, the subsequently inserted therapeutic devices.

Both the needle/suture deployment housing 22 and 23 and the receptor housing 24 and 25 can be slidably coupled to the body of the obdurator 31 and may be secured at a center portion of the housing by attachment members 90 and 92 fitted in attachment slots 91 and 93 that runs along the long axis of the device.

Figure 6B:
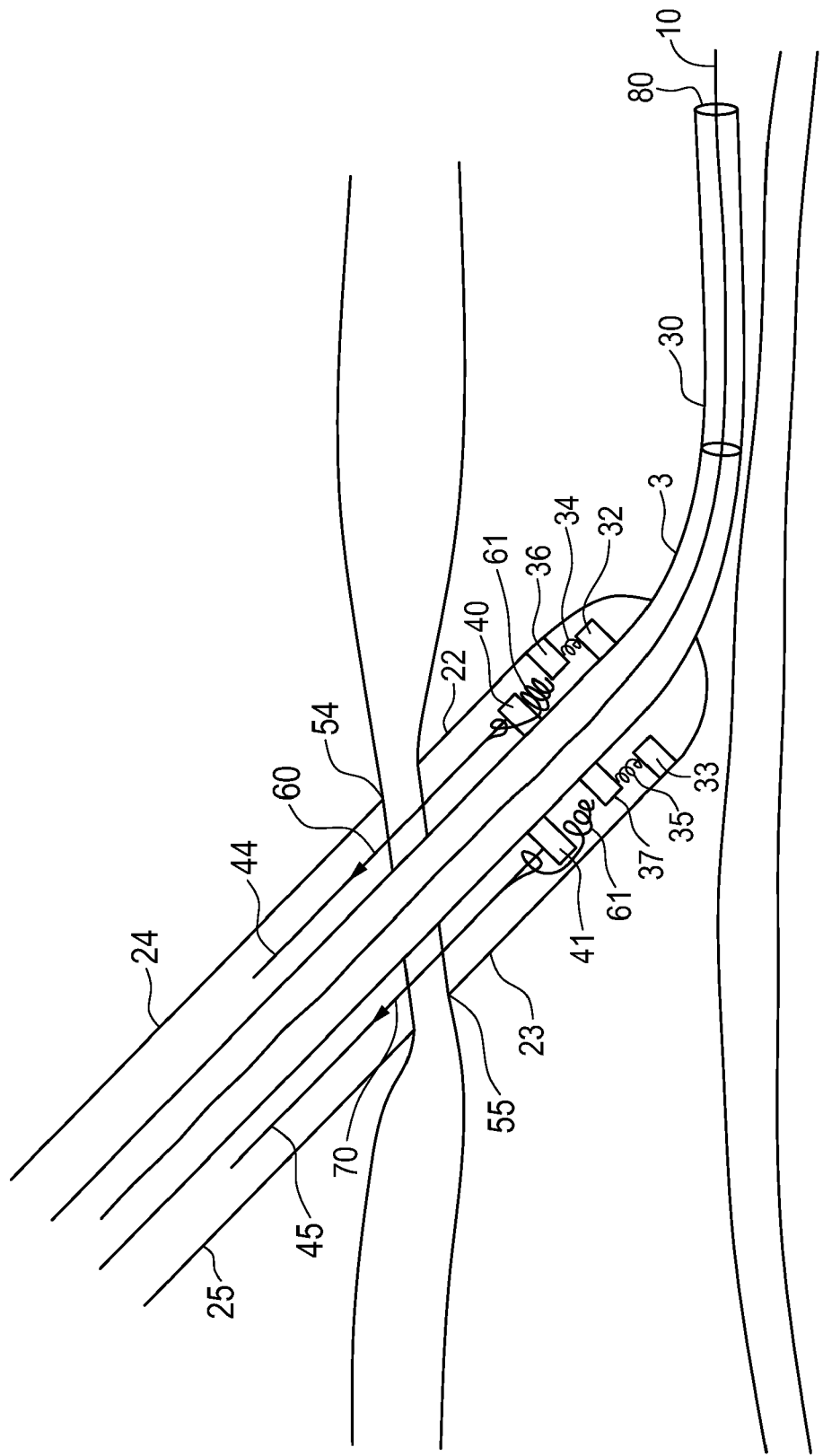

With reference to FIG. 6b, activation of the suture deployment mechanism occurs when the suture receptor housing 24 and/or 25 are advanced and compressed against the suture deployment housings 22 and/or 23. The receptors 24 and 25 may advance, capture and compress the vessel tissue in the slot 54 and 55. If the receptors 24 and 25 are further advanced, the deployment housing 22 and 23 can slide distally on the obdurator 20. The distal movement of the deployment housings 22 and 23 can occur when the leaf springs 34 and 35 which hold the housings 22 and 23 proximal are compressed. The brackets 32 and 36 can move towards one another and the needle tips can becoming unhoused once the deployment housing 22 and 23 have moved a sufficient distal distance. The needles can be pushed through the vessel tissue, enter the receptors and become fixed compressively.

Deployment of sutures 61, 63, 65 and 67 can occur by withdrawing the needle receptor 24 and 25 with the needles embedded. The needles which were held in the brackets 40 and 41 compressively at their distal ends are pulled out and advance with the receptor housings 24 and 25 proximally, come up and out of the vessel pulling their respective sutures 61, 63, 65 and 67 behind them and can be further pulled with the receptor housing up and out of the vessel access tool where the sutures 61, 63, 65 and 67 can be manually accessed and the needles removed. The length of suture 61, 63, 65 and 67 required will approximate the depth of the vessel access tool with a little additional suture (preferably 2 cm or more) required to encircle the obdurator within the artery and provide sufficient length outside the body for manipulation. Arrangements can be made to store suitable amounts of suture by making the housing suitably large and/or creating a recess the body of the dissecting obdurator sufficient in size.

The receptors 24 and 25 are withdrawable along the slots 91 and 93, pulling out the needles and unraveling the sutures 61, 63, 65 and 67 as they go. The sutures 61, 63, 65 and 67 are pulled out of their housings 22, 24 because the housings 22, 24 are secured to the body 31 along its central axis and compressibly fitted along their edges such that there is friction but no obstruction to withdrawing the sutures 61, 63, 65 and 67.

Once the needles are withdrawn, the sutures 61, 63, 65 and 67 remain in place around the dissecting obdurator. The dissecting obdurator is withdrawn and the vessel is reloaded with sheaths and other devices as needed. The sutures can be used to spread the vessel edges to make way for the withdrawal of the dissecting obdurator 20 if needed.

Figure 7A:
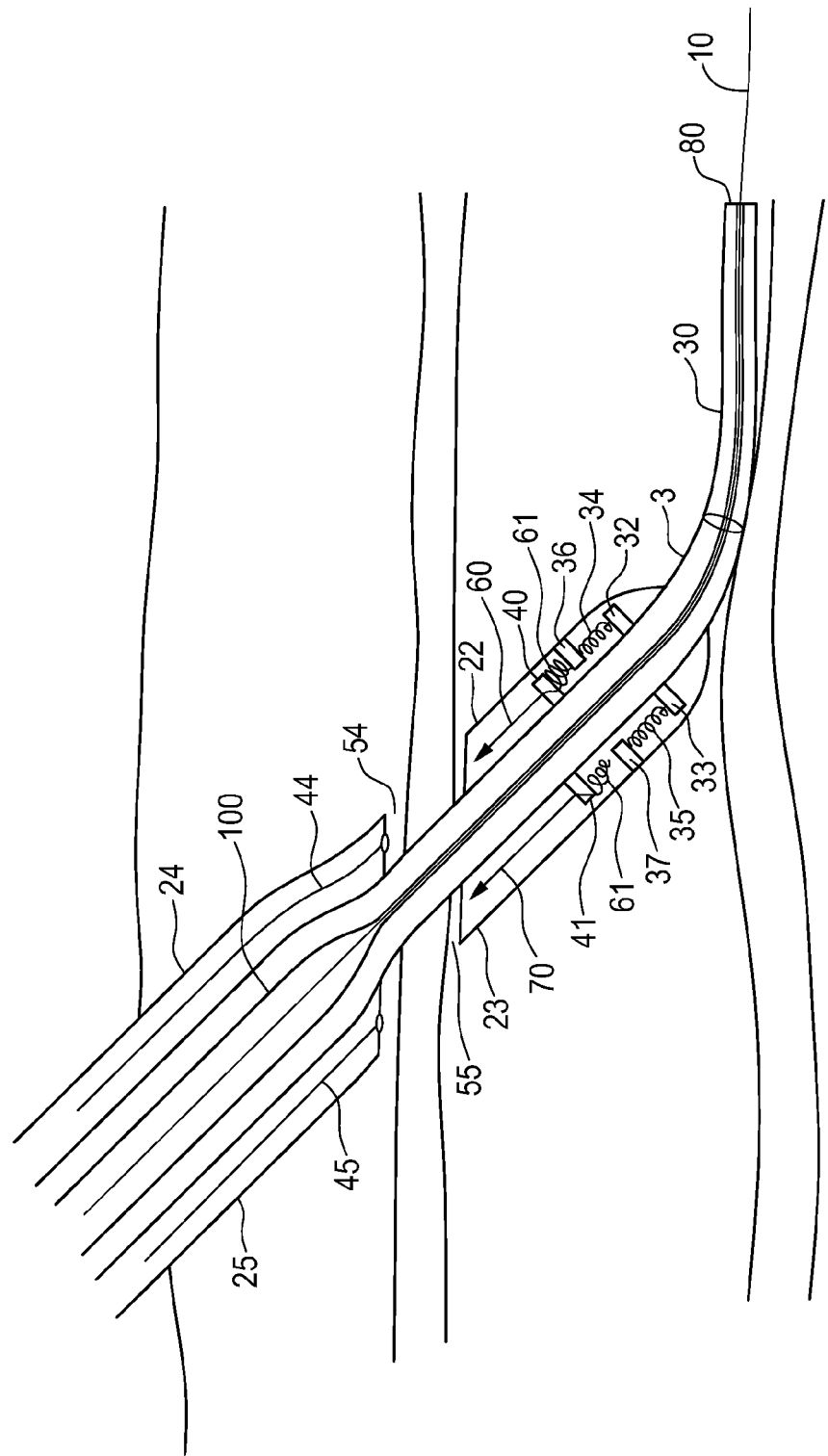
Figure 8:
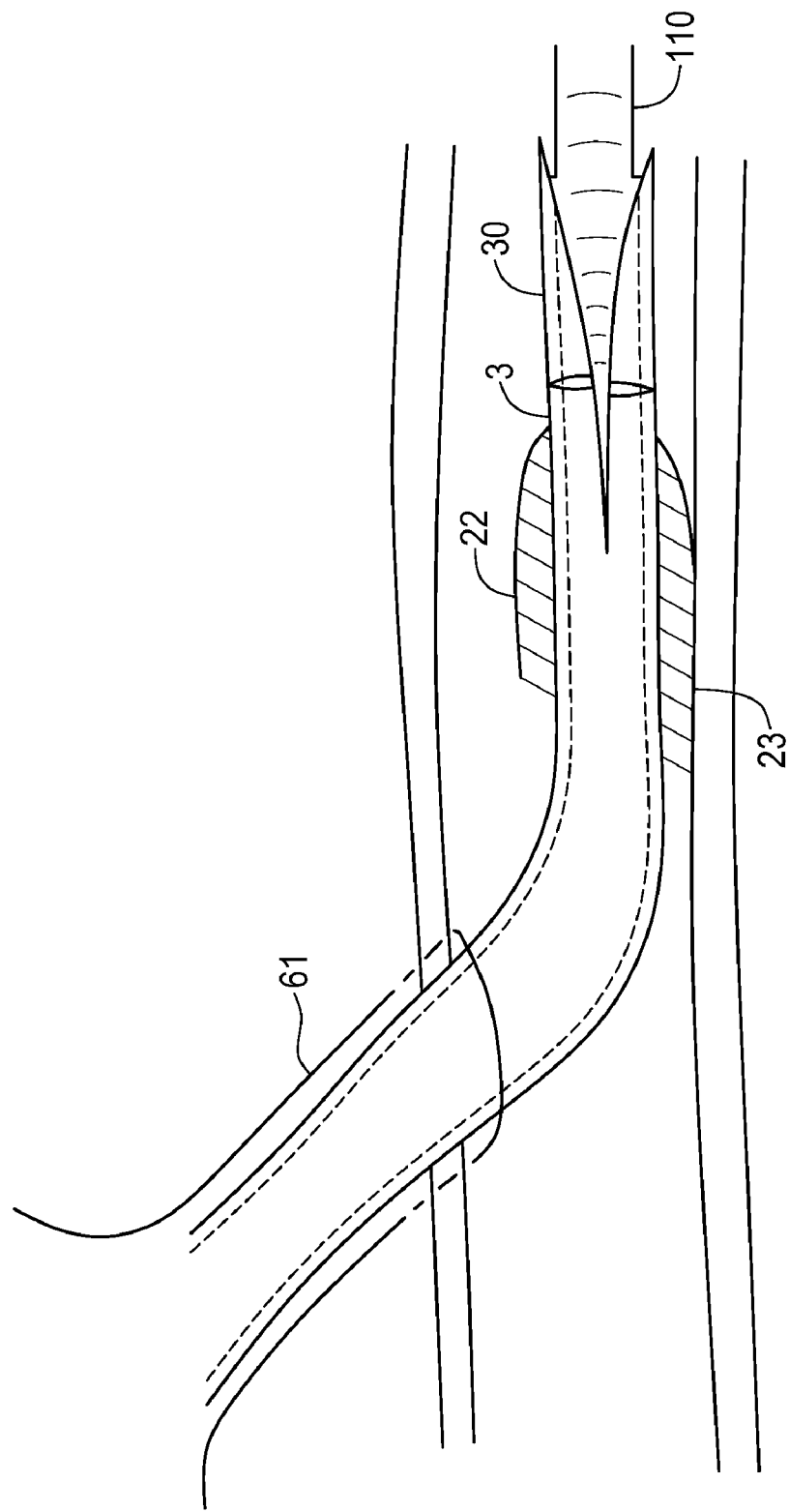
FIG. 8 illustrates an embodiment of a splittable dissecting obdurator used as sheath in a side view.

Alternately, in other embodiments with reference to FIGS. 7b, 9a and 9b, the obdurator may be splittable, such that a splitting tool 100 may be used to open a seam 81 running down the middle of the dissecting obdurator 20 and the obdurator left in place and used as a sheath with devices run through it as shown in FIG. 8.

The vessel opening is closed at the end of the procedure by manually forming a knot and using a knot pusher of known construction following removal of all devices.

As previously described, the vessel access tool 1 is intended to create access to an artery minimally invasively. Initial access to the vessel can be gained by the Seldinger technique. Following placement of a balloon tipped guidewire 11, the vessel access tool 1 is delivered in its compressed state over the guidewire 11 using the viewing mandrel 8 to determine whether the vessel wall has been located. Upon location of the vessel wall, the access tool 1 arms are spread, preferably to a diameter just larger than the hole to be created and the viewing mandrel 8 removed from the guidewire 11. A small incision in the skin may need to be made to in order to accommodate the vessel access tool 1. While the vessel access tool 1 is illustrated as going in over the guidewire 11, in other embodiments, the access tool 1 could go in over needle.

Next, the dissecting obdurator 1 is loaded onto the guidewire 11. The dissecting obdurator is advanced until the tapered section 38 enters the artery and begins to dissect the artery wall. At this time, it is important to center the obdurator 20 and adjust for any bias in the initial needle stick.

As the dissecting obdurator 20 enters the vessel but before the tapered section 38 is engaged with the tissue, the obdurator 20 should be oriented such that a transverse arteriotomy will be created. As previously discussed, this can be accomplished visually but also by using the selective flexibility feature of the device. The operator of the obdurator 1 will notice that less resistance will be encountered when the obdurator 20 is properly oriented. Because there is less bending resistance in the proper orientation, the obdurator may naturally assume the proper orientation if allowed to rotate freely. Alternatively, by sensing the physical resistance to rotation, the proper alignment of the obdurator 1 can be determined. Once properly oriented, the obdurator 1 can be advanced, the taper 38 engaged and dissection commenced. Once the taper 38 has fully penetrated the vessel wall, the housings 22, 23 will be advanced into the vessel. Extra resistance will be felt by the movement of the housings 22, 23 through the vessel wall. When the housing 22, 23 advances past, the vessel wall with engage with the vessel wall capture ports 54 and 55. At this point, advancement should be stopped and the suture deployment mechanism may be activated. The user can slidably advance the suture receptor housing 24 or 25 and compresses the suture deployment housing 22 or 23. Upon compression, the needles push through the vessel tissue and enter the receptors where they can become fixed compressively.

The user can secure the sutures 61, 63, 65 and 67 by withdrawing the needle receptor 24 and 25 with the needles embedded. The receptors 24 and 25 can be withdrawn along the slots 91 and 93, pulling out the needles and unraveling the sutures 61, 63, 65 and 67 as they go. Once the needles are withdrawn, the sutures 61, 63, 65 and 67 remain in place around the dissecting obdurator.

The vessel opening can be closed at the end of the procedure by manually forming a knot(s) in the sutures 61, 63, 65 and 67 and using a knot pusher of known construction following removal of all devices.

Numerous variations on this method and apparatus are contemplated. One frequent problem in vessel access procedures is the presence of excess amounts of blood in the operative field. In order to address this issue, the access tool spreader arms 2 and 3 may be hollow such that suction holes, preferably on the inside, at the distal ends of the spreader arms 2 and 3 are in communication with a medical suction element such that blood is automatically removed from the field.

An additional issue may be the reliability of the capture of the vessel walls edges in the vessel capture slots. Referring now to FIGS. 7a-b, it can be seen that it may be advantageous to expand the dissecting obdurator 20 with an internal dilating element 100 by expanding the body in the short cross sectional axis and creating a tighter fit between the vessel wall tissue and the vessel capture slot. This embodiment has the advantage of being more reliable at capturing the vessel wall in the slot where it can be sutured shut. If the wall is not captured in the slot, the closing procedures cannot be properly performed. In this embodiment, the obdurator dilation mandrel 100 as shown in FIG. 9a is inserted in the split to open obdurator lumen 81 and, as advanced, splits open the obdurator expanding it as shown in FIGS. 7a and 7b. Insertion of the mandrel follows insertion of the dissecting obdurator into the artery and prior to deployment of the sutures.

In another embodiment, the needle/suture receptors 24 and 25 are lined with a suture capture frame 160 that wraps around the dissecting obdurator. The suture capture frame 160 is shown in FIG. 10 and may be made of metal, polymer or a bioresorbable polymer. The frame is located just distal to the needle receptor ports and fits snugly around body of the dissecting obdurator 31. When deployed, the needles penetrate the tissue, pass through the holes 170, 172, 174, 176, 180, 182, 184 and 186 in the frame and into the needle receptor ports in the housings. The frame holes are sized sufficiently small such that they compressibly capture and immobilize the sutures in the frame. The frame 160 is biased closed such that it holds the hole shut once the obdurator and subsequent devices are removed from it. It is releasable from the receptor such that it is left behind on the surface of the vessel as a permanent implant. Because the sutures are compressibly held in place, it may not be necessary to create a knot or use a knot pusher to close the opening.

Many combinations of needles, sutures and capture mechanisms are disclosed in the prior art designed for deployment post-procedure from round or substantially circular needle deployment mandrels. Combinations of these needle, suture and capture assemblies may be amenable to configuration with a flat dissecting obdurator and deployable at the start of a procedure are possible alternate embodiments. In one embodiment, the proximal receptor ports are replaced with a mesh capture material as shown in U.S. Pat. No. 5,417,699 which is hereby incorporated by reference.

Alternate embodiments of the dissecting element are also possible. A flat mandrel that makes a deformable hollow round obdurator flat is one possible embodiment and has the benefit of providing for a more consistently round sheath in the event that the obdurator is also used as a splittable sheath as described above. The flat mandrel might be in place during insertion of the obdurator and removed in a final step in order to provide for access though the obdurator.

Alternately, the obdurator may be splittable, such that a splitting tool 100 may be used to open a seam 81 running down the middle of the dissecting obdurator 20 and the obdurator left in place and used as a sheath with devices run through it as shown in FIG. 8.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the flowing claims reflect, inventive aspects lie in less than all features of any single foregoing disclosed embodiment.

What is claimed is:

1. A medical tool comprising:
   an access tool; and
   a dissecting obdurator for placement at least partially within a lumen of the access tool, the dissecting obdurator comprising:
      a body having a height dimension measured and a width dimension perpendicular to the height dimension, the height dimension is two or more times the width dimension;
      a tapered portion coupled to a distal end of the body, the tapered portion having a first edge and a second edge; and
      a selectively flexible tip coupled to a distal end of the tapered portion, the selectively flexible tip being more flexible bending in the axis of the width dimension than bending in the axis of the height dimension.

2. The medical tool of claim 1 further comprising:
   a guidewire in a guidewire lumen extending through the selectively flexible tip.

3. The medical tool of claim 1 further comprising:
   a viewing mandrel for placement at least partially within the lumen of the access tool, the viewing mandrel being optically clear and including a bulbous tip for cannulation and enhanced light collection.

4. The medical tool of claim 1 wherein the tip includes a plurality of flexibility notches.

5. The medical tool of claim 1 wherein the tip has a circular cross section and a diameter between about 2-5.0 French Catheter Scale (Fr).

6. The medical tool of claim 1 wherein the height of the elongated body is between about 12-30 French Catheter Scale (Fr).

7. The medical tool of claim 1 wherein the first edge and the second edge that are sharp surfaces having a radius of curvature of less than 1 mm for dissecting a vessel of a body.

8. The medical tool of claim 1 wherein the dissecting obdurator includes a needle and suture deployment module for deploying needles and sutures and a needle and suture receptor module for receiving the needles and the sutures from the needle and suture deployment module.

9. The medical tool of claim 8 wherein the needle and suture receptor module is separated from the needle and suture deployment module by a vessel access slot.

10. The medical tool of claim 9, further comprising:
    an expansion mandrel for increasing the width dimension of the body of the dissecting obdurator.

11. The medical tool of claim 1 wherein the access tool comprises:
    a first spreader arm having an elongated shape;
    a second spreader arm having an elongated shape;
    an actuator coupled to the first spreader arm and the second spreader arm; and
    a lumen defined by a space between the first spreader arm and the second spreader arm.

12. The medical tool of claim 11 wherein the first edge is adjacent to a first inner surface of the first spreader arm and the second edge is adjacent to a second inner surface of the second spreader arm.

13. The medical tool of claim 11 wherein the first spreader arm includes at least one suction hole for removing blood from an area around the vessel.

* * * * *